(12) United States Patent
Prins et al.

(10) Patent No.: US 7,545,496 B2
(45) Date of Patent: Jun. 9, 2009

(54) SUPPORT WITH A SURFACE STRUCTURE FOR SENSITIVE EVANESCENT-FIELD DETECTION

(75) Inventors: Menno Willem Jose Prins, Rosmalen (NL); Johannes Joseph Hubertina Barbara Schleipen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 533 days.

(21) Appl. No.: 10/561,469

(22) PCT Filed: Jun. 14, 2004

(86) PCT No.: PCT/IB2004/050895

§ 371 (c)(1),
(2), (4) Date: Dec. 20, 2005

(87) PCT Pub. No.: WO2004/113886

PCT Pub. Date: Dec. 29, 2004

(65) Prior Publication Data

US 2007/0146717 A1    Jun. 28, 2007

(30) Foreign Application Priority Data

Jun. 25, 2003 (EP) .................... 03101893

(51) Int. Cl.
G01N 21/00 (2006.01)
G02B 6/26 (2006.01)
G02B 6/42 (2006.01)

(52) U.S. Cl. .................... 356/344; 385/30; 356/244; 356/445

(58) Field of Classification Search .......... 356/335–344, 356/224, 244, 445
See application file for complete search history.

(56) References Cited

U.S. PATENT DOCUMENTS

| 3,975,084 | A | * | 8/1976 | Block .......................... 356/335 |
| 4,815,843 | A | * | 3/1989 | Tiefenthaler et al. ........ 356/128 |
| 4,839,902 | A | * | 6/1989 | Guch, Jr. ...................... 372/70 |
| 5,156,976 | A | * | 10/1992 | Slovacek et al. .............. 436/64 |
| 5,327,225 | A | * | 7/1994 | Bender et al. ................ 356/445 |
| 5,340,715 | A | * | 8/1994 | Slovacek et al. ............... 435/6 |
| 5,468,606 | A | * | 11/1995 | Bogart et al. .................. 435/5 |
| 5,939,709 | A | * | 8/1999 | Ghislain et al. ............. 250/216 |
| 5,994,150 | A | * | 11/1999 | Challener et al. ........... 436/518 |
| 6,300,638 | B1 | * | 10/2001 | Groger et al. ............ 250/458.1 |

(Continued)

FOREIGN PATENT DOCUMENTS

DE    196 28 002 C1   12/1997

OTHER PUBLICATIONS http://www.olympusmicro.com/primer/java/tirf/penetration/index.html.*

*Primary Examiner*—L. G Lauchman
*Assistant Examiner*—Jarreas C Underwood

(57) ABSTRACT

A support structure, such as an optical disc, is designed having surface structures formed on one or more surfaces of the support to enable formation of evanescent fields in a medium adjacent to the surface structures and allow for detection of optically-active substances within the evanescent fields in the medium. The surface structures may be formed in one or more areas on the surface of the support. The surface structures may have inclined surfaces that are inclined with respect to a general plane of the support surface, and form wedge structures or symmetric pyramidal structures, for example.

26 Claims, 11 Drawing Sheets

U.S. PATENT DOCUMENTS

| | | | |
|---|---|---|---|
| 6,317,206 B1 * | 11/2001 | Wulf | 356/317 |
| 6,406,777 B1 * | 6/2002 | Boss et al. | 428/209 |
| 6,897,436 B2 * | 5/2005 | Smolyaninov et al. | 250/234 |
| 6,929,943 B1 * | 8/2005 | Quapil et al. | 435/287.1 |
| 7,154,598 B2 * | 12/2006 | Montagu et al. | 356/244 |
| 2002/0003623 A1 * | 1/2002 | Tajima et al. | 356/311 |

* cited by examiner

SUPPORT WITH A SURFACE STRUCTURE FOR SENSITIVE EVANESCENT-FIELD DETECTION

The present invention is concerned with a support, in particular an optical disc, with a surface structure for the detection of at least one optically-active substance within the evanescent-field at one surface of the support, whereby the surface structure allows the generation of an evanescent-field in a medium adjacent to the surface structure. The invention also concerns a device employing such a support with a surface structure, in particular an optical disc and uses of the support with a surface structure and the device.

Heterogeneous binding assays are routinely used in chemical and biological test systems to evaluate the capacity of a target compound or ligand contained within a test specimen, e.g. a fluid, to bind to immobilized capture probes. Such assays are used in all areas of chemistry, biochemistry or biology where the interaction between two or more chemical entities is examined. In particular in biology and biochemistry many processes, including, for example, regulative processes, signal transduction, the formation of larger functional complexes or the immune response depend on the specific interactions between proteins or between proteins and nucleic acids. A large variety of heterogeneous assay formats have been developed using many different approaches for detection of binding. For example, such assays are used for the diagnosis of diseases by immobilizing antibodies, which bind to a disease-related antigen on a surface and detecting the antigen contained in a sample solution. The presence or absence of the antigen is then indicative of the specific disease. Similar assays are also performed in approaches of directed evolution, wherein a variety of slightly different compounds immobilized at different positions on a surface are contacted with the same target and those compounds which show the strongest interaction with the target are selected for further analysis (e.g. by mass spectrometry) and further modification.

To detect binding of a ligand to a capture probe a variety of methods have been used, which include electrochemical methods like, for example, potentiometric methods, and radiation-based methods including, for example, detection of fluorescence, light scattering or radioactivity. Some of these detection methods require the introduction of a label, which can be specifically detected. For example, such label can be attached to the capture probe and a variation of the signal upon binding of the ligand to the labeled capture probe is detected. It is also possible to label the ligand and detect the signal of the bound ligand upon binding to the capture probe. Another assay format involves labeling of a third component, which specifically binds the ligand and, thus, is recruited via the unlabeled ligand to the capture probe. The later assay format is called sandwich assay and is most commonly used, for example, in enzyme linked immunosorbent assays (ELISA). Other assay formats, which have equally been employed in the prior art include unbinding, displacement and competition assays. Depending on the way of measurement of the binding or unbinding a variety of labels have been used in the prior art including, for example, radioactive labels, fluorescent labels, scattering labels, or enzyme labels.

In a typical embodiment of a binding-type assay format the medium containing a labeled ligand is removed after incubation with the immobilized capture probes leaving behind labeled ligand only at those capture probes, to which the ligand has bound. In a next step, for example, when employing fluorescently labeled ligands the labels are now excited by light of a wavelength specific for the label and the fluorescence generated at each capture probe is measured. Usually in this arrangements the light used for excitation is directed onto the surface coated with the capture probes from above and the emitted fluorescence is detected.

Another approach for measuring fluorescence, which has been used in the prior art is the use of an evanescent-field for excitation of a fluorescent label. An evanescent-field is formed if a light beam is directed at an angle $\beta$ at the interface of two materials, i.e. a translucent support material and a probe material, typically a liquid or a gas, and if the quotient of the refractive index of the two materials, i.e. the liquid sample or gas ($n_{exit}$), which lies adjacent to the translucent support material ($n_{entrance}$), through which the light beam is directed is smaller than the sinus of the angle $\beta$. This situation leads to total internal reflection (TIR) of the light beam at the interface and the formation of an evanescent-field in the liquid or gas, wherein the depth of the field formed at the interface depends on the respective refraction indices, the angle, and the wavelength of the light. The use of an evanescent-field for the detection of fluorescence in an immune assay is disclosed in DE 196 28 002 wherein a light source is directed at an angle at a plane base-plate on top of which a capture probe is arranged to which a biological sample can be applied, however, the format disclosed in DE 196 28 002 in which a laser light source is directed at an angle at a plane surface covered by a second plane plate with a cut out section, which forms a cuvette-like compartment for holding the sample, is not suitable for high throughput applications, which require the read out of binding signals from many different locations on a surface. DE 196 28 002 does not disclose adaptations of the evanescent-field detection to high throughput applications, which would involve the excitation of different capture probes immobilized in different areas. The problem of the technology disclosed in DE 196 28 002 is in part the following: To address many different spots on the surface on the plane base plate the light beam of the laser, which has a fixed position, would have to be moved over the surface of the base plate in a scanning fashion, however, this would change the angle of the light beam with respect to the plate during the scanning and, thus, the depth of the evanescent-field at each scanned point. In addition the strength of the evanescent-field, i.e. the depth of the of the field formed, is small due to relatively small angles of inclination of the light source, which can be achieved in the set-up disclosed in DE 196 28 002.

This problem is solved by the provision of a support with a surface structures comprising inclined planes, which allow the generation of an evanescent-field at many different locations on the surface structure, while keeping the angle of the light beam used for generation of the evanescent-field essentially constant and at small or no inclinations with respect to the plane of the support, and moving either the support with a surface structure comprising the inclined plane(s) relative to the light source or moving the light source or the light beam relative to the support with a surface comprising the inclined plane(s).

FIG; 1A shows an arrangement in which light directed at the surface of the support at an angle which is not sufficient to allow total internal reflection in accordance with an embodiment of the present invention;

Figure 1A:
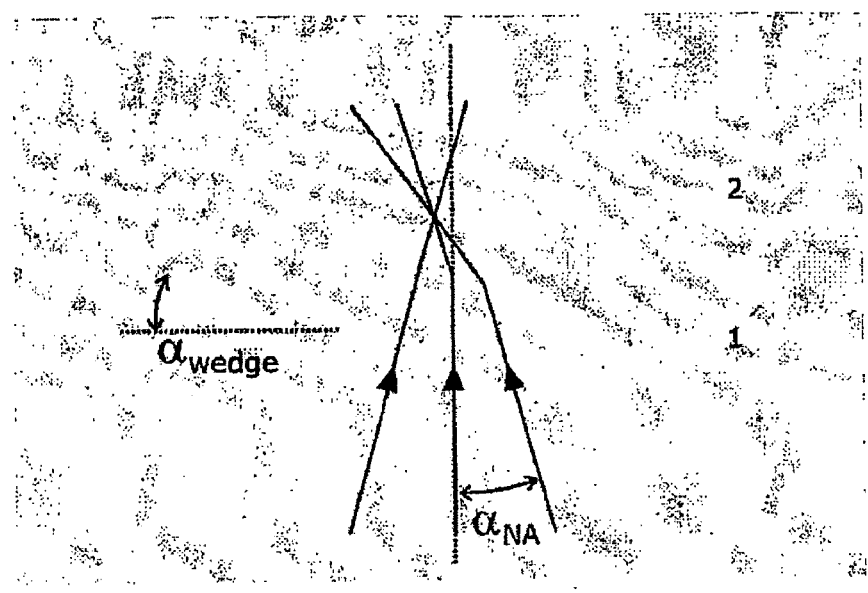
FIG. 1B shows an arrangement in which total internal reflection (TIR) can be achieved at an interface between a support and a medium in accordance with an embodiment of the present invention.

Therefore, in one embodiment the present invention provides a support with a surface structure for the detection of at least one optically-active substance within the evanescent-field, in particular for the detection of binding and/or unbinding events, at one surface of the support, in which in at least one area a plane of said surface is inclined with respect to the plane by an angle $\alpha_{wedge}$ from about 10° to about 85°. A support with the above delineated surface features will be capable of generating (an) evanescent-field(s) on the surface of the support once light is shone onto the surface even if the light is directed at the surface in a perpendicular fashion.

The term "support" as used in the present invention refers to a material having at least two surfaces which are essentially parallel to each other. The distance between the two surfaces is preferably between 0.1 mm and about 1 cm, and most preferably between about 0.5 mm and 3 mm. The material of the support is at least at the surface structure comprising the inclined plane(s) translucent. Preferably the support is made of essentially translucent material. Appropriate materials include without limitations polymers like, for example, poly carbonates, polyethylenterephtalat, cyclic olefinic polymers, and other materials such as glass and quartz. Supports within the meaning of the present invention, thus, include, for example, glass slides or plates and optical discs. Preferably the support is an optical disc. The support can be made entirely out of one material, can have a layered structure combining different materials or can have areas within the support made out of different materials.

The size and form of the support is not particular limited. It preferably is between 0.1 mm$^2$ and 400 cm$^2$, more particular between 0.2 mm$^2$ and 200 cm$^2$, most preferably between 1 mm$^2$ and 150 cm$^2$. The support can have in a preferred embodiment a circular, rectangular, square or triangular shape. Most preferably the support has a circular shape.

The term "inclined plane" refers to a section of the surface of the support, which is inclined with respect to the general orientation of the surface of the support and which is essentially flat, flat or curved. In a preferred embodiment the surface of the plane is essentially flat or flat and in the most preferred embodiment the surface of the plane is flat.

In a preferred embodiment the angle at which the plane of the surface is inclined with respect to the surface of the support is from about 15° to about 75°, more preferably from about 25° to about 65° and most preferably from about 35° to about 55°. The appropriate angle, which leads to evanescent-field formation will in part be determined by the inclination of the light beam with respect to the surface of the support, which is in a preferred embodiment determined by the numerical aperture of the focussing objective lens directing a light beam at the inclined plane in a reader device.

In the curved embodiment of the inclined plane the plane has different angles with respect to the surface of the support at each point along the curve, however, the angle of each point on the curve is preferably within the above indicated range and preferred subranges, thus allowing evanescent-field formation along the curved inclined plane.

The suitable angle $\alpha_{wedge}$ necessary to lead to total internal reflection (TIR) of the light directed at the surface, which in turn leads to the generation of an evanescent-field in the medium adjacent to the disc, i.e. on the surface of the support, depends on the refractive index of the translucent material of the optical disc ($n_{support}$), on the refractive index of the medium adjacent to the disc ($n_{medium}$), which preferably contains a ligand, and on the angle $\alpha_{NA}$ between the light beam and the normal of the surface of the support. The inclination of the light beam ($\beta_{TIR}$) relative to the normal of the inclined plane is the sum of $\alpha_{wedge}$ and $\alpha_{NA}$ ($y_{TIR}=y_{wedge}+y_{NA}$). Total internal reflection and evanescent-field formation occurs when $y_{TIR} \geq \arcsin(n_{medium}/n_{support})$.

In most cases the medium containing the sample to be measured will be a water-based solution or dispersion and, since water has a refractive index of about 1.33 the refractive index $n_{medium}$, i.e. the liquid comprising the sample, will be between 1.3 and 1.7, and preferably about 1.33. If a sample with a refractive index of 1.33 is used total internal reflection and evanescent-field formation will occur when the refractive index $n_{support}$ of the material of the support is larger than 1.33 and if the angle $\beta_{TIR}$ fulfills above criterion for TIR. However, in some cases the liquid can be replaced by gas at the time of measurement and then the refractive index of $n_{medium}$ will be about 1.0. Therefore, in order to allow TIR and evanescent filed formation to occur at the support-gas interface the refractive index of the support material has to be larger than 1.0. Accordingly, in a preferred embodiment the refractive index $n_{support}$ of the material of the support is larger than 1.0 and smaller than 2.0 and preferably larger than 1.33 and smaller than 1.9 and most preferably between about 1.4 and about 1.8. In particular if the support of the present invention is its preferred embodiment, i.e. an optical disc, then the refractive index $n_{support}$ is preferably larger than about 1.33 and smaller than about 1.9 and more preferably between about 1.4 and about 1.8.

Taken together, the refractive index of the medium containing a sample adjacent to the support typically varies in the range of 1.0 to 1.7 and, therefore, a wide variety of support materials can be selected in order to generate an evanescent-field on the medium side of the medium-support interface depending on the chosen $\beta_{TIR}$. In the preferred embodiment of the support of the present invention, i.e. the optical disc, a support with the indicated optical properties can be made from a variety of materials including, for example, polycarbonates (PC) or cyclic olefinic polymers. However, it is not required, that the entire support, preferably the entire disc is made out of material having the above indicated refractive and optical properties. It is possible to use this material only in those parts of the support, preferably the disc comprising a surface structure with one or more inclined planes.

Current methods of microstructuring of the surfaces of materials, in particular optical discs, allow the formation of several billions of indentions (pits) to store data and a similar technology can be used to form within the surface of the optical disc further inclined planes capable of generating an evanescent-field in a medium once light is directed at them. Therefore, the support of the present invention comprises at least one area with such inclined plane(s) preferably between 10 areas and 1,000,000 areas. In medical diagnostic applications the support, preferably the disc will typically have between 1 and 100 different areas, however, for some applications like, for example, pathogen fine-typing or DNA polymorphism determination the number of areas will preferably be between 1.000 and 100.000. Preferably the areas comprising an inclined plane are separated from each other by a surface area which is either plane or structured with channels, raised regions, trenches or structures to fluidically separate one or more areas of the support, preferably the disc, from one or more other areas of the support. The areas comprising one or more inclined planes can in a preferred embodiment be structured itself to form, for example, one or more channels, which extend radial from the center of the support, preferably the disc, or be structured to form one or more channels arranged azimuthal around the center of the support, preferably the disc.

The surface size of an inclined plane depends on the depth of an inclined plane, its inclination and its extension along the surface of the support. The term "depth" in this context means the distance between two theoretical planes, which run parallel to the surface of the support, and in which one plane touches the lower end of the inclined plane and the other touches the upper end of the inclined plane (see also "δ" in FIG. 2). The depth of an inclined plane is preferably between about 0.1 µm and about 2 mm, more preferably between about 2 µm and about 100 µm, more preferably between about 4 µm and about 10 µm. The extension of the inclined plane along the surface is limited only by the size of the area comprising (the) inclined plane(s). This area can be structured, for example, like a radial, spiral or azimuthal channel and can comprise along the surface structures separating two or more inclined planes from each other or one inclined plane can extend along the complete area. The size of the inclined plane ranges in a preferred embodiment from about 100 nm$^2$ up to a size larger than the projected surface area of the support. This is due to its inclination and occurs, for example, if the inclined plane is arranged in a spiral covering the complete surface of the support. More preferably the inclined plane will have a surface area of between about 1 µm$^2$ and about 2 mm$^2$ and even more preferably between about 10 µm$^2$ and about 1 mm$^2$.

The area on the support comprising the inclined plane and possibly additional inclined planes adjacent to the first inclined plane has in a preferred embodiment a surface area of about 100 nm$^2$ up to the entire surface area of the support. More preferably the area on the support comprising the inclined plane(s) will have a surface size of between about 100 µm$^2$ and about 40 mm$^2$ and even more preferably between about 1 mm$^2$ and about 20 mm$^2$. The total surface size will depend on the dimensions of the support and in a preferred embodiment on the diameter of the disc. The size of the support is not particularly limited and can vary in a wide range. In a preferred embodiment the support will be structured as a disc and will have a diameter of between about 2 cm and about 30 cm and more preferably the diameter will be equivalent to the diameter of a CD/DVD.

In a preferred embodiment of the invention the surface of the support comprising one or more inclined planes is covered by a top plate. This serves to prevent efflux of medium, undesired mixing and/or evaporation of liquid from the surface of the support. The distance between the top plate and the surface is preferably between about 1 µm and about 2 mm and more preferably between about 30 µm and about 500 µm. The top plate can connect with, for example the upper edge of the inclined planed, raised regions or other surface structures in some or all areas of the surface of the support to form separated reaction regions, channels or the like.

Other structures which are included in preferred embodiments of the support comprise feed or purge lines, fluid inlet and outlet ports, valves, mixing chambers, passive and active switches, sample pretreatment elements such as filters, beads or columns comprising appropriate matrices like, for example, anionic or cationic exchange resins, immuno-affinity resins or liquid storage compartments like, for example, reagent storage compartments, wash fluid storage compartments or waste storage compartments.

Fluid actuation within the support can be managed by a variety of means known in the art including but not limited to over- or underpressure, centrifugal forces, capillary forces, peristaltic forces, magnetic forces, electrical forces (e.g. electrophoresis or dielectrophoresis).

Beside the above outlined structures other structures can also be present on surface of the support or embedded in the support like, for example, pit-patterns as in CD and DVD (re-)writable and/or ROM technology or masks and/or reflective coatings which render part of the disc non-transmissive and which can be made, for example, from metal like aluminum, silver or gold. These structures can serve, for example, as information storage (read/write) and/or tracking device for the optical system when reading the support, in particular if the support is structured in its preferred embodiment, i.e. as an optical disc. The information can, for example, include instructions for the reading device on how to perform the reactions and on the settings, e.g. the wavelength, needed for reading the support. It is also envisioned that the results and other process or sample data are stored on the support during or after the measurement process. Tracking devices like, for example, pits are preferably arranged in the vicinity of an inclined plane and are more preferably embedded in the support material beneath the inclined plane to allow easy alignment of the light beam of a reading device and localization of the individual inclined plane(s). This is particularly useful if a light beam is used for reading the support, which has a focal point beneath the inclined plane(s) on the surface of the support, preferably within the support (see, for example, FIG. 3). Such tracking devices can be disposed, for example, on the internal interface of two layers of the support as is known from pits in single or multilayer CDs or DVDs.

Figure 3:
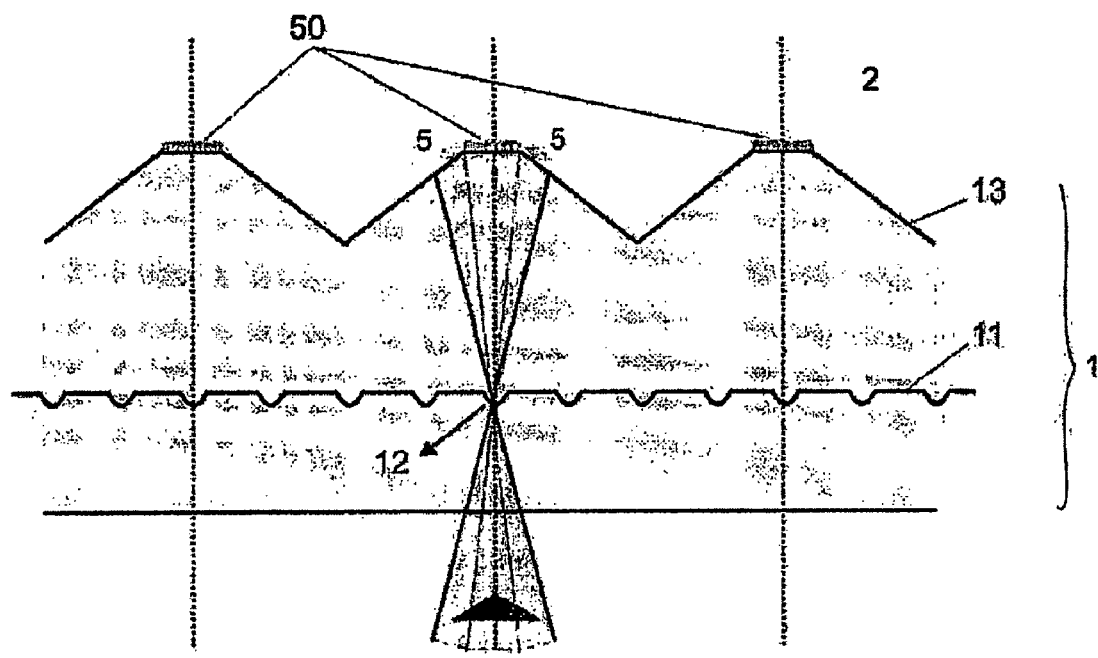
FIG. 3 shows an example in which an additional tracking layer is provided in the support which allows the correct alignment of the light with the inclined planes on the surface of the support in accordance with an embodiment of the present invention.

In a preferred embodiment the support can be further structured in such that the area on the surface of the support, which comprises the inclined plane(s), contains one or more additional planes adjacent to the first inclined plane(s) (see, for example FIG. 1). Preferably the second plane has a larger inclination, however, with an opposite sign, than the first inclined plane preferably in the range between 60° and 90° and is arranged in such that a "wedge" structured is formed. In a particularly preferred embodiment the second plane is arranged adjacent to the first inclined plane in a symmetrical fashion leading to the formation of a pyramidal structure within the area (see, for example FIG. 5). The angle of inclination and the preferred angels of inclination of the two symmetrically inclined planes are as outlined above for the first inclined plane. In this arrangement evanescent-fields can be elicit on the surfaces of both planes of the pyramidal structure thereby increasing the energy of the evanescent-field within one measuring area. Preferably in this embodiment two light beams having an identical angle (or angles in cases where the light in the light beam is not parallel but, for example, focused) with respect to the normal of the support, however, with an opposite sign are directed at the pyramidal structure. Each beam will undergo TIR at one of the two symmetrical planes and will be refracted and transmitted into the medium at the other plane. In this arrangement transmission of light, which does not undergo TIR might occur and in some embodiments it might be necessary to inhibit light transmission into the medium adjacent to the support to improve measuring accuracy. This can be achieved, for example, by applying reflective or absorbing material to the support, preferably to the surface of the support in appropriate areas. Such reflective materials comprise, for example, aluminum, gold or silver. The above described two inclined planes can also be separated from each other by one or more intermediate planes, which are preferably arranged parallel to the plane of the surface. Such intermediate planes can, for example, reflect light, which otherwise would be transmitted into the medium. FIG. 3 shows, for example, an arrangement with three planes, in which the first and the second plane have a pyramidal structure with an intervening third reflective plane.

The inclination of the second plane can also be chosen in such that it totally reflects a beam which already has been reflected by TIR at the first inclined plane. This second TIR event will lead to the formation of a second evanescent-field within one measuring area and depending on the angles of inclination of the first and second plane two evanescent-fields of varying or identical depths can be created within one measuring area. Preferably in this embodiment only one light beam, preferably with an angle with respect to the plane of the support, is directed at the surface of the support. It will undergo TIR at the first plane and will be refracted and transmitted into the medium at the second plane, however, the beam internally reflected at the first plane will undergo a second TIR at the second plane. This arrangement will reduce the amount of light transmitted into the medium.

In a further embodiment the support of the present invention is also structured on the second surface, i.e. the surface opposite to the surface comprising one or more areas with inclined planes. The surface on the support directly opposite the inclined planes can be either plane with respect to the plane of the support or inclined. The inclination can be identical or less than the inclination of the plane at which the optically-active substance is detected. Furthermore, the opposite surface of the support can also comprise structures needed for fluid distribution, sample preparation, sample application, fluid storage or sample removal as outlined above. Preferably those further structures do not interfere with light directed at the inclined plane used for generation of an evanescent-field.

In a preferred embodiment the support of the present invention is provided with at least one capture probe which is attached to the inclined plane. The term "capture probe" comprises any chemical compound that is directly or indirectly attachable to a surface. In a preferred embodiment the capture probe is selected from the group comprising proteins, in particular antibodies, receptors, enzymes, signaling proteins or fragments thereof, peptides, nucleic acids, in particular single stranded DNA, double stranded DNA and RNA, mono and polysaccharides, nucleic acid analogs, in particular PNA and small molecules.

The term "peptide" comprises polypeptides of a length between 2 and 50 amino acids, while the term "proteins" comprises polypeptides of a length of 50 and more amino acids. The amino acids of which the peptides or proteins are composed can be naturally or non-naturally occurring amino acids and can be of D- or L-configuration.

The term "small molecules" comprises organic compounds of any structure smaller than 2000 g/mol. Such molecules are preferably used in drug development, since they are small enough to pass from the intestines into the blood of a patient and can, thus, be orally administered.

The capture probe can be attached directly or indirectly to the inclined plane(s) on the surface of the support while the attachment can be through covalent and/or non-covalent links. The support surface itself can be functionalized for this purpose with, for example, a hydrogel, a self-assembled monolayer, a surface allowing chemisorption or by physisorption. For covalent linking of capture probes to the surface of the support the surface of the inclined plane can be provided with groups capable of cross-linking with the capture probe like, e.g. epoxy-groups, which react with amino-groups in peptides or proteins. The skilled artisan knows a wide variety of chemical residues that allow the formation of covalent links between a (functionalized) support surface and capture probes. Similarly the capture probe(s) itself can be provided with reactive groups capable of forming a covalent or a non-covalent link with the surface of the support in particular in the region of the inclined plane(s). Attachment can also be indirect by, for example, coupling biotin to the capture probe and coating the surface of the support in particular the inclined plane(s) with protein A, which is capable of binding to biotin with high affinity. This mode of attachment leads to an indirect non-covalent attachment of the capture probe. A great variety of additional suitable attachment means are well known in the art. Preferably, after the linking process the capture probe forms a dense layer on the medium side of the inclined plane, which is then referred to as a "capture layer". The capture layer preferably covers the complete inclined plane, however, it can also be patterned to any shape on the inclined plane including spots, which are then referred to as "capture spots".

The chemicals necessary to attach the capture probe to the surface of the inclined planes as well as the capture probe(s) itself can be applied to the support surface by a variety of means including, for example, printing and spotting. Such directed application provides the additional possibility to lay down reagents and capture probes in a predetermined pattern on the surface of the support.

In general one type of a capture probe will be attached to one inclined plane, however, in a further embodiment of the support of the present invention two or more different capture probes are attached next to each other on the same inclined plane. This embodiment is particular preferred, if inclined planes with large surface areas are arranged on the support, which than contain several different capture spots or capture layers within one extended inclined plane. Depending on the type of assay, which is to be performed, in some embodiments a mixture of two or more capture probes is attached to one inclined plane.

In a further preferred embodiment the support of the present invention comprises reagents needed for sample preparation and/or measurement like, for example, buffers, negative and positive controls, enzymes and/or enzyme substrates. These can be contained in the device as wet and/or dry material. In particular if dried material is provided then this will preferably be rehydrated prior to use by the addition of an appropriate liquid including, for example, water or buffer.

In a particular preferred embodiment of the support of the present invention the support is an optical disc. An optical disc is an essential circular structure, which is preferably made out of polycarbonate. It preferably has a centered contact means, which allows contact with a reading device like, for example, a hole.

In a further aspect the present invention is also concerned with a kit comprising a support, preferably an optical disc, and at least one reagent. Reagents within the meaning of the present invention comprise any chemical compound necessary to perform or facilitate a reaction on the disc. Preferably reagents are selected from negative controls, positive controls, buffers, enzymes, labeling agents and/or enzyme substrates.

A further aspect of the present invention is a device for the detection of at least one optically-active substance within the evanescent-field at one surface of a support comprising: a) at least one light source, and b) at least one detector means wherein the at least one light source is arranged in such that it is opposite to the surface of a support where detection occurs once the support is placed in the device.

The detector means can be positioned on the same side or opposite to the light source. In a preferred arrangement at least one detector means is arranged on the same side and more preferably the detector means is arranged to detect any radiation emitted back from a support placed in the device towards the light source. This is the usual arrangement of a silicon PIN or CMOS-detector and a CD/DVD-player, where a splitter is placed in the light path of the laser diode, which directs the light reflected back towards a detector. The same arrangement can be used in the present invention, which allows the integration of light source and detector within a small unit which can be easily moved in x or y direction with respect to the surface of the support, preferably the optical disc. However, the detector can also be placed on the opposite side of the light source, i.e. on the side of the medium, which leads to a separation of the two light systems. In this case appropriate means must be provided to assure exact alignment of the light source and the detector means. This is necessary to allow the assignment of the measurement of radiation elicited by the evanescent-field to a particular inclined plane.

The light source preferably generates essentially monochromatic light. Thus, the light source is preferably a laser and more preferably a laser diode. The light source can be further provided with appropriate filters to eliminate, for example, light of undesired frequencies or to polarize the light. Preferably the laser is tunable to different wavelengths in case when evanescent-fields of different depths are required and/or in cases when different frequencies of excitation are needed for the detection of the optically-active substances, in particular for the detection of binding and/or unbinding events. Alternatively or additionally further light sources generating light of a different wavelength can be included in the device of the present invention. These light sources are in a preferred embodiment arranged in such that light of all light sources is directed at the same point on the surface of the optical disc. This allows the simultaneous measurement of, for example, the competition of two differently labeled ligands for binding to (a) capture probe(s).

In a preferred embodiment the angle $|\alpha_{NA}|$ of the light ($\alpha_{NA}$ is the angle between the normal of a support inserted into the device and the light) is larger than 0°. This can be achieved by inclining the light source relative to the support or by "inclining" the light by optical means like, for example, by an objective lens or by a mirror. In a preferred embodiment an objective lens is placed in the light path, which focuses the light beam. This leads to an inclination of the light with respect to the surface of the support, which increases towards the perimeter of the lens (see, for example, FIG. 4 and FIG. 7). Depending on $\alpha_{wedge}$ and $\beta_{TIR}$ TIR will occur for all light, which has an inclination $\alpha_{NA} \geq \beta_{TIR} - \alpha_{wedge}$. This critical angle at which TIR will start to occur, i.e. $\alpha_{NA} = \beta_{TIR} - \alpha_{wedge}$, is also called $\alpha_{TIR}$. All light refracted in the objective lens to be directed at the support at an angle of at least $\alpha_{TIR}$ will, thus, be reflected by TIR and an evanescent-field will be formed. However, all light directed at the support at an angle of less than $\alpha_{TIR}$ will be refracted when passing through the support-medium interface.

Figure 4:
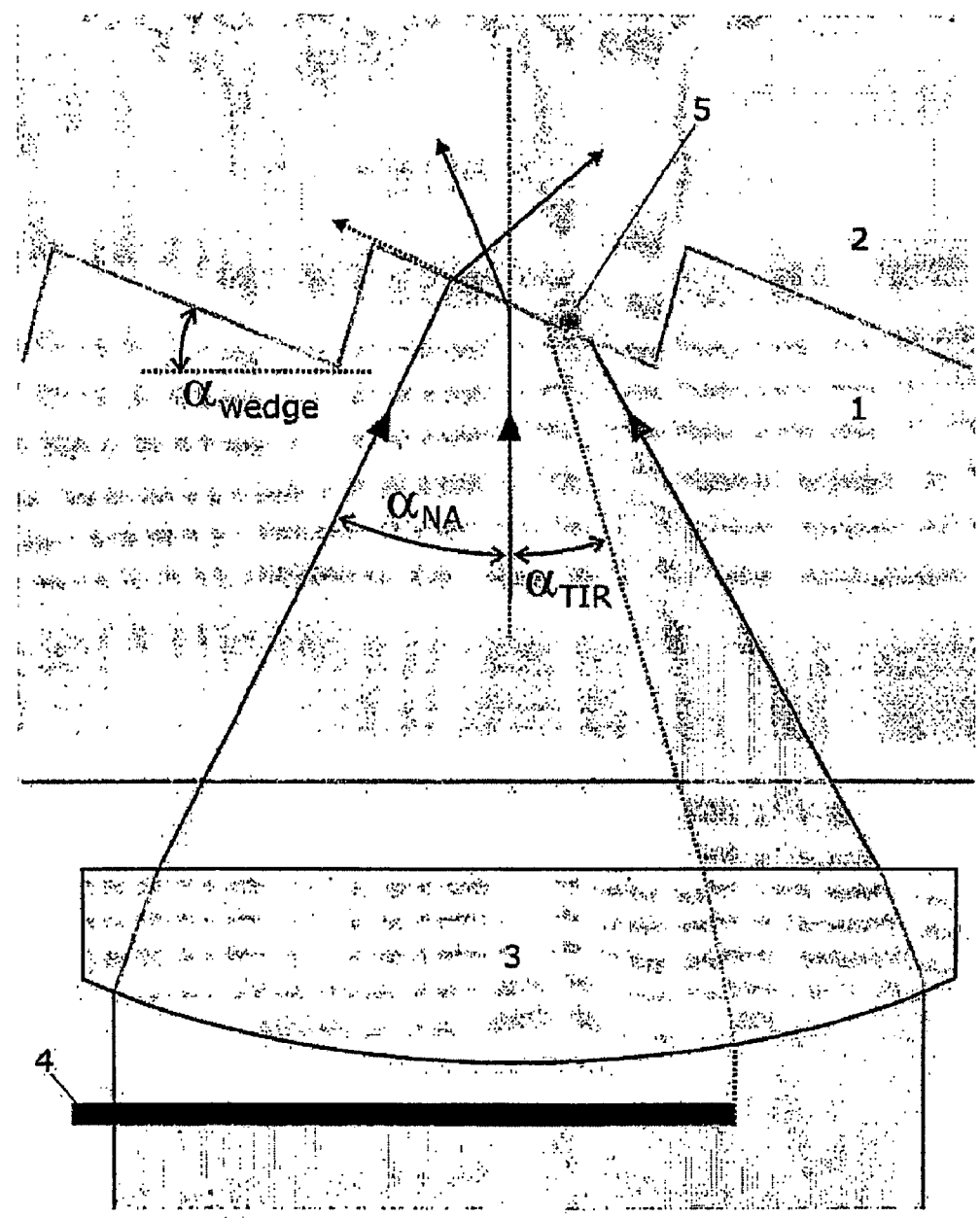
FIG. 4 shows an example where the disc/medium interface is being irradiated by a focused beam generated by an objective lens in accordance with an embodiment of the present invention.
Figure 5:
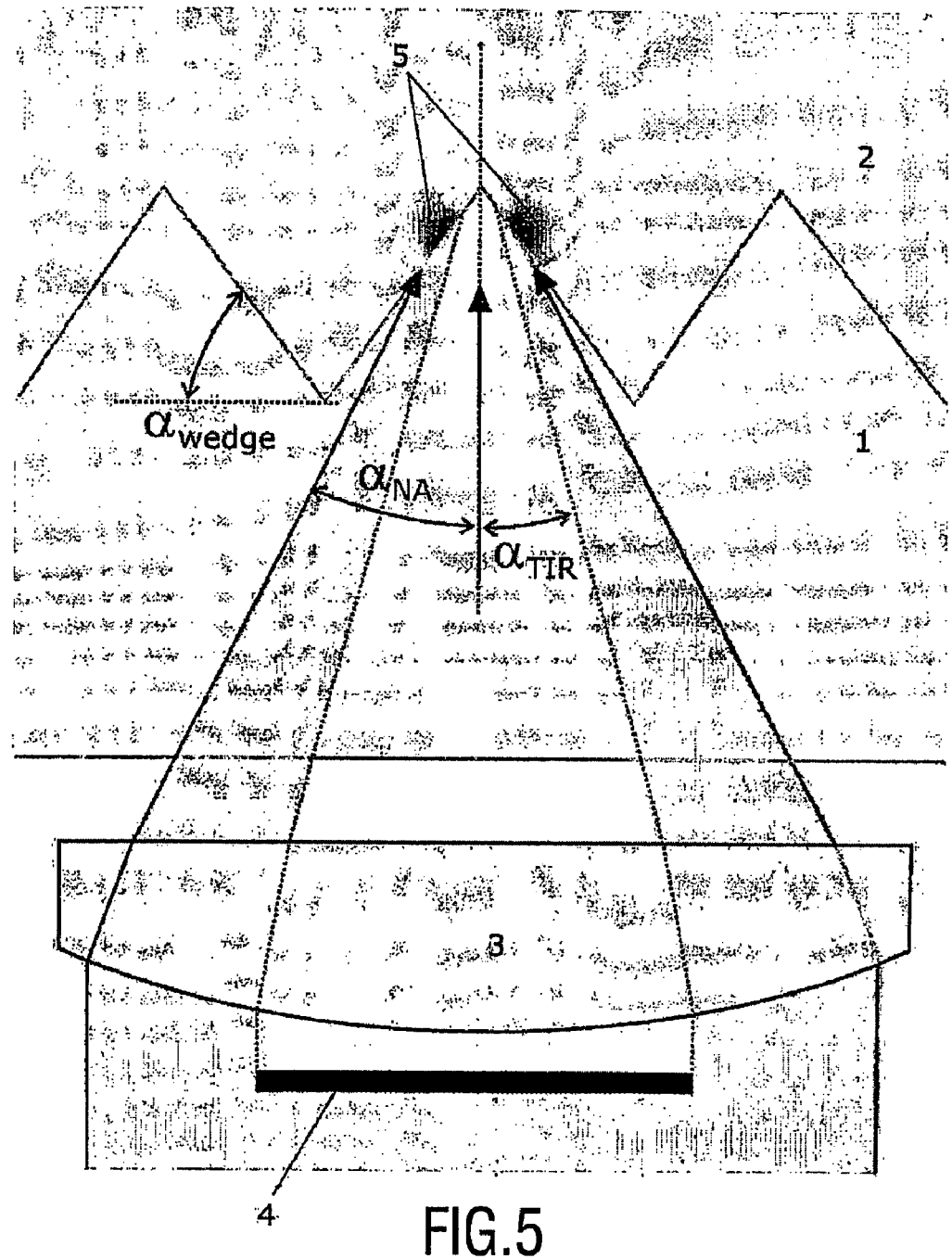
FIG. 5 shows an example where the wedge shaped structure has been replaced by a symmetric pyramidal shaped structure in accordance with an embodiment of the present invention.
Figure 6:
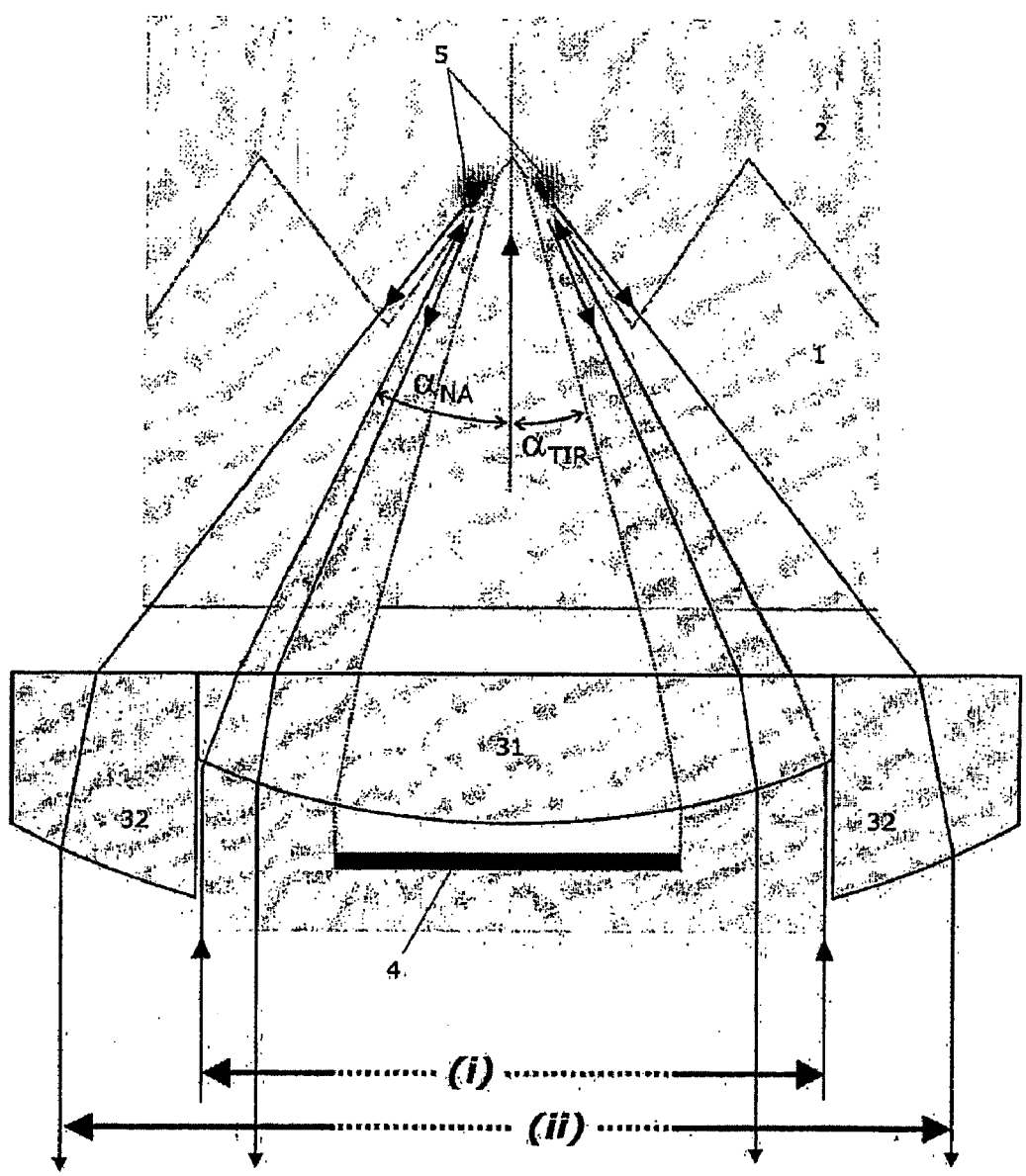
FIG. 6 shows the same set-up as FIG. 5, however the objective lens has been modified such that a central part lens, which is partly covered by an obstructive mask, provides the light beam eliciting the evanescent-field and is used for the generation of tracking signals in accordance with an embodiment of the present invention.

In a preferred embodiment all light having an angle of less than $\alpha_{TIR}$ is blocked from being directed at the support by a mask which is placed in the light path (see, for example, FIG. 4-6). In some embodiments this mask will essentially completely block light from one side of the objective (see, for example, FIG. 4) or will be arranged to essentially block all light with an angle of $\alpha_{TIR}$ less than (see, for example, FIG. 5). The mask can be made of completely non-transmissive material or of a dichroic or polarization sensitive material (see, for example, FIG. 10). The latter having the advantage that while all light directed at the support will elicit TIR, i.e. no light is directed at the support with an angle smaller than $\alpha_{TIR}$, the radiation, e.g. the fluorescence, elicited by the evanescent-field is not blocked by a solid mask and more light can reach the detector leading to a more sensitive measuring set-up.

In another preferred embodiment one or more additional lenses are arranged in concentric circles around a central part lens. This composite lens is positioned between the light source and the support. The additional lens(es) are made out of material with a higher refractive index than the central part lens (see, for example, FIG. 6). While the center lens is used to direct light at the support at an angle $\geq \alpha_{TIR}$ the second or further lens, having a higher refractive index than the center lens, provides a wider acceptance angle for collecting the radiation emitted by the ligand and, thus, this set-up has a higher sensitivity than the single lens set-up. This embodiment preferably includes a mask as outlined above to block essentially all light with an angle less than $\alpha_{TIR}$.

In addition to the features of the optical system outlined above a variety of additional optical elements like, for example, collimators, splitters, dichroic splitters or the like can be included in the optical system of the device of the present invention. The device of the present invention can comprise features which are well known in the art from CD/DVD players or writers, in particular it can comprise parts or all of the optical set up including objective lenses, light sources, detectors, filters, splitters or the drive and actuation devices employed in such players or writers.

The detector means can be any means capable of detecting radiation, preferably a PIN diode or CMOS-device. The choice of the suitable detector means depends on the radiation which needs to be detected, which in turn depends on the optically active substances, in particular on the label comprised in the optically active substance. Consequently, if the detection of the optically active substance, in particular the detection of binding or unbinding events depends on the detection of fluorescence, which has been stimulated by the evanescent-field, than the detector should be capable of detecting fluorescence of the relevant wavelength. If the signal is light scattered by the label or reflected (as in surface-plasmon-based detection), then the detector means should be capable of detecting light of the same wavelength as emitted by the light source. In a preferred embodiment of the device of the present invention one or more filters are arranged in front of the detector, which, for example, in case of the detection of fluorescent light can be a filter with a broad absorption spectrum and/or a polarizing filter. These filters serve to exclude scattered light of the light source, which could decrease the sensitivity of the assay.

In a further preferred embodiment of the device of the present invention the wavelength of the light source, the inclination of the light with respect to the normal of the disc $\alpha_{NA}$ and the angle $\alpha_{wedge}$ of the inclined plane(s) of the surface of the support is (are) selected in such that the depth (d) of an evanescent-field, which is formed in the medium containing the sample, is between 10 nm and 1 μm, preferably between about 20 nm and 200 nm. The depth of an evanescent-field, which is caused by light of a given wavelength, can be calculated according to the following equation:

$$d = \frac{\lambda}{2\pi} * \frac{1}{\sqrt{n_{support}^2 * \sin^2(\alpha) - n_{medium}^2}}$$

whereby "$\lambda$" is the wavelength of the light, "$n_{support}$" is the refractive index of the material of the support in the light path and "$n_{medium}$" is the refractive index of the medium comprising the optically active substance, in particular a ligand, which is to be measured, for its binding or unbinding to the surface of the support, "$\alpha$" is the angle of the light with respect to the normal of the interface between the two materials, i.e. the inclination of the plane, and "d" is the depth of the evanescent-field in the medium. Using the above indicated formula the skilled person can easily select the depth of the evanescent-field based on the wavelength of the light emitted by the light source, the angle of inclination of the light with respect to the normal of the support and/or the angle of inclination of the inclined plane. The smaller the depth of the evanescent-field the less optically active substances are detected, which are not bound to the inclined plane but rather are contained within the medium. The selection of very small depths d in which the evanescent-field is formed leads to excitation of optically active substances only, if they are very close to the interface. If the depth of the evanescent-field is selected to only extend over the length of the capture probe and the molecule bound to the capture probe such selection would allow the detection of binding events on the surface of the support without removal of the medium containing unbound optically active substances and/or label since primarily optically active substances, which are bound to the surface of the support, e.g. to the attached capture probe, will be effected by the evanescent-field, e.g. excited to fluoresce.

However, in some embodiments of the support of the present invention and its use it is desired to generate an evanescent-field, which has a depth that also extends to molecules which are near the surface but not directly attached to the surface. This allows the measurement of the concentration of unbound optically active substance(s) and/or unbound labels in the medium. The concentration of the optically active substance(s) and/or labels in the medium, which binding or unbinding is to be measured, affects the amount and dynamics of the binding of the optically active substances and, thus, is important to know. This is particularly the case when quantitative measurements and not only qualitative measurements are to be carried out.

In the embodiment of the present invention in which the light is focused in the device on the support (see, for example, FIG. 2) and, thus, the light beam reaches the inclined plane under a variety of angles, the length of the section of the inclined plane at which TIR occurs, i.e. the TIR active area length ($l_{TIR}$), can be determined by the following formula:

$$l_{TIR} : \frac{\sin(\alpha_{wedge}) \cdot \sin(\alpha_{TIRMAX} - \alpha_{TIR})}{\sin(\alpha_{wedge} - \alpha_{TIRMAX}) \cdot \sin(\alpha_{wedge} - \alpha_{TIR})} \cdot |x|$$

in which "$\alpha_{TIRMAX}$" and "$\alpha_{TIR}$" are the bounding angles for which TIR occurs at the interface of the inclined plane(s) formed on the surface of the substrate and the medium. The steepness of the inclined plane is defined by "$\alpha_{wedge}$", "x" is the distance of the focal point from the upper edge of the inclined plane, also termed the "defocus" introduced in the system. In this embodiment "defocus" is needed in order to obtain reflection (TIR for angles of the light $\geq \alpha_{TIR}$) and refraction (for angles of the light $<\alpha_{TIR}$) at the surface of the inclined plane. If no defocus would be introduced (x=0), the support would be sampled in the near field of the focus where the incoming wave front is perpendicular to the surface of the support. In this case the angles $\alpha_{TIRMAX}$ and $\alpha_{TIR}$ would be virtually zero and no TIR would occur.

Preferably x is a few focal depths of the focussing system:

$$x \approx \sigma(1) \cdot \frac{\lambda}{NA^2},$$

and preferably between 1 and 100 μm, more preferably between 2 and 50 μm and most preferably between 4 and 20 μm. x can have a negative or positive sign, i.e. the focal point can be located beneath or above the surface of the support.

The depth of the inclined plane "δ", which is required to accommodate the possible TIR active area length for a given defocus x can be determined as follows:

$$\delta = \left\{ \frac{\sin(\alpha_{wedge}) \cdot \sin(\alpha_{TIRMAX})}{\sin(\alpha_{wedge} - \alpha_{TIRMAX})} - 1 \right\} \cdot |x|$$

In a further aspect of the present invention the device of the present invention further comprises the support of the present invention. The device is adapted with suitable actuation devices like, for example, servo motors or piezo elements to move the support, for example, in x or y direction or in circular fashion. However, it is also possible to move the light source and/or the detector relative to the support, for example, in an x or y direction. In a particular preferred embodiment the support is an optical disc. The disc can be rotated in the device around an essentially centered contact means preferably a hole in the disc, which is used to center the disc in the device.

In this embodiment the light source and/or the detector means can be stationary or move relative to the disc, preferably laterally.

A further embodiment of the present invention is the use of a support of the present invention or a device of the present invention for the detection of at least one optically-active substance within the evanescent-field at one surface of the support, in particular at a surface of an optical disc. A preferred use is the detection of binding or unbinding of an optically active substance contained within a medium to one or more inclined planes of the surface of the support by an evanescent-field. In a preferred embodiment of the use of the present invention the optically active substance is detected by fluorescence, optical scattering and/or reflectance modulation.

The term "optical active substance" comprises any chemical entity capable of reflecting, refracting, adsorbing or scattering an evanescent-field or being excitable to fluores or phosphores by an evanescent-field. The optical active substance either possesses this activity alone like for example, GFP-proteins or possesses it by virtue of one or more labels, which can be directly or indirectly attached. A wide variety of labels is known in the art like, for example, fluorochromes like, for example, FITC, Cy3, Cy5, rhodamine, fluorescein or quantum dots or auto-fluorescent proteins like, for example, green fluorescent protein (GFP) or variants thereof or metal particles in particular gold or silver spheres (nanoparticles), or up-converting phosphors.

Label(s) can also be attached to the capture probe or additional components that may bind to the optical active substance and/or the capture probe.

In a preferred embodiment the optical active substance comprises a ligand attached to a label.

The term "ligand" comprises any chemical entity capable of being bound by a capture probe as defined above. In particular the term ligand comprises nucleic acids and nucleic acids analogs, including DNA, RNA, PNA and the like; proteins and peptides, including enzymes, transcription factors, signaling molecules and signaling molecule receptors, structural proteins and receptors; mono of poly saccharides; single cells, cell aggregates and tissue fragments, including all human, animal or plant cell types, preferably hemapoetic cells like, for example, T-cells, B-cells, macrophages, dendritic cells, platelets, red blood cells; bacteria including without limitation *Acidaminococcus, Acinetobacter, Aeromonas, Alcaligenes, Bacillus, Bakteroides, Bordetella, Branhamella, Brucella, Calymmatobacterium, Campylobacter, Cardiobacterium, Chromobacterium, Citrobacter, Clostridium, Corynebacterium, Edwardsiella, Enterobacter, Enterococcus, Erysipelothrix, Escherichia, Eubacterium, Flavobacterium, Francisella, Fusobacterium, Haemophilus, Helicobacter, Klebsiella, Lactobacillus, Legionella, Listeria, Micrococcus, Moraxella, Morganella, Neisseria, Pasturella, Peptococcus, Peptostreptococcus, Plesiomonas, Propionibacterium, Proteus, Providencia, Pseudomonas, Salmonella, Serraria, Shigella, Staphylococcus, Streptobacillus, Streptococcus, Veillonella, Vibrio* and *Yersinia* species; viruses including without limitation adenovirus, enteric adenovirus, adeno associated virus (AAV), influenza virus, parainfluenza virus, orbuvirus, coronavirus, encephalomyocarditis virus, enterovirus, ECHO virus (enteric cytopathogenic human orphan virus), coxsackie A group virus, coxsackie B group virus, cytomegalovirus, varicella-zoster virus, papilloma virus, baculovirus, picorna virus, rubella virus, mumps virus, encephalitis virus, SSPE virus, polio virus, measles virus, stomatitis virus, hepatitis virus, rhinovirus, REO virus, rotavirus, vaccinia virus, pig Oasky's disease virus, and retro viruses such as human imununodeficiency virus (HIV) and herpesvirus; protozoans; and small molecules as defined above.

In a further embodiment of the invention the evanescent-field is not (or not only) used to excite labels attached to ligands but rather to selectively out-couple light generated near the surface structure.

In a preferred embodiment the support of the present invention or the device of the present invention are used in diagnostic applications. Diagnostic applications typically involve the removal of a specimen from a patient or an animal. Examples of such specimens are blood, urine, sperm, vaginal secretion, stool, sputum, tissue, cells, lymph or the contents of the gastrointestinal tract. The specimen can be applied directly to the support or can be further processed externally by, for example, filtration, enzymatic treatment, mechanical and/or chemical disruption to isolate, e.g. single cells, DNA only, RNA only and/or protein only. In some embodiments the specimen is subcultured prior to the processing step in order to increase the amount and/or detectability of a particular ligand within the specimen. The specimen or the further processed specimen can be mixed with a variety of reagents like, for example, buffers, preservatives or stabilizing agents. Usually the specimen or the further processed specimen is applied to the support as a solution or suspension. However, one or more of the above processing steps, which can be carried out externally, can also be integrated into the support, i.e. occur inside the support. In a preferred embodiment the specimen, in particular a blood sample, is directly applied to the support, preferably to the disc and processed inside the support prior to measuring the binding or unbinding of a ligand comprised in the sample. Such a series of processing steps can, for example, include the lysis of cells, purification and concentration of DNA or RNA, in case of RNA additionally reverse transcription, amplification of target DNA or cDNA, hybridization with a DNA capture probe, selective washes. An embodiment, in which a large number steps of sample preparation and analysis are carried out within the support, preferably the disc is termed "lab-on-a-chip" or "lab-on-a-disc". The skilled artisan is well aware of a large variety of processes which can be used to prepare (a) ligand(s) for later detection. The skilled person also knows how to select the appropriate sequence of a series of disruption, preparation, purification, concentration, washing and/or amplification steps, which are necessary to allow detection of (a) given ligand(s) within a sample. As pointed out above the support of the present invention can include a variety of additional structures, which allow to carry out the desired processing steps.

In diagnostic applications ligands are detected, which are indicative of a disease or a predisposition to a disease. Such ligands include without limitation DNA, RNA or proteins of microorganisms, in particular pathogens, including bacteria, viruses and protozoans as well as intact microorganisms or fragments thereof, and tissues or fragments thereof, cells, antigens, DNA, RNA, peptides or proteins, in particular antibodies in its natural or mutant form of a patient or animal. Based on the ligand that needs to be detected a suitable capture probe can be selected by someone of skill in the art. For cell, virus, protein, peptide or antigen detection suitable capture probes are, for example, antibodies or binding fragments or derivatives thereof. For DNA or RNA suitable capture probes are, for example, DNA or RNA. For nucleic acid detection by hybridization it is usually necessary to heat the support comprising the nucleic acid ligand and the corresponding capture probe. The heating step can be carried out outside of or within the device of the present invention. Thus, the device of the present invention can in a preferred embodiment also include a means of controlling the temperature of the support, preferably a heating means, which allows the hybridization of nucleic acids to take place within the device. Such means of controlling the temperature are known in the art and comprise, for example, Peltier elements and heat sinks. If desired this temperature control means can be used to carry out other reactions alternatively, prior or subsequent to the hybridization, which require a change of temperature, like for example, polymerase chain reactions (PCR), enzymatic digestions or reverse transcriptions. Typically, a target DNA or RNA is amplified via a PCR-reaction prior to hybridization with DNA capture probes. It is also envisioned that the light source of the device itself can be utilized as a heating means alone or in addition to above temperature control means. Light can also be used to photochemically activate or cross-link molecular species present in the device in particular on or above the surface of the support like, for example, to cross-link two DNA strands one of which is attached to the surface of the support.

The incubation of the ligand(s) containing medium with the capture probe(s) can be followed by one or more wash or reaction steps with, for example, buffers, enzyme substrates and/or secondary reagents like, for example, labeled antibodies. The skilled artisan is aware of a variety of appropriate buffers and reagents and knows, for example, how to select for a given capture probe-ligand binding pair, i.e. for a DNA/DNA interaction or for a protein/protein interaction, buffers suitable to remove unspecifically bound ligands. The washing and/or reaction steps can be followed in some embodiments by removal or displacement of liquid medium in the support, preferably in the measuring area by gas. The gas can be any gas or mixture of gases and is preferably, air or an inert gas like, for example, argon or nitrogenous gas. The, thus, lowered refractive index of the medium adjacent to the support will allow TIR to occur at lower $\beta_{TIR}$ and, consequently, at lower $\alpha_{NA}$ and/or $\alpha_{wedge}$. This in turn will in particular in embodiments of the invention using a mask in front of an objective lens allow the use of smaller masks and, thus, the generation of a higher energy evanescent-field on the surface of the support and, consequently, a higher sensitivity.

To detect optically-active substances in the evanescent-field formed on the surface of the support, in particular to determine the binding or unbinding of a ligand to the surface of the support, more particularly to the capture probes, a wide variety of assay formats well known in the art can be employed like, for example, binding assays, unbinding assays, sandwich assays displacement assays and competition assays. The appropriate assay format will depend on the type of analysis to be performed, the ligand and the capture probe and can be readily chosen by someone of skill in the art. The binding and/or unbinding events in one of the above assaying formats can be detected by a single measurement, repeat measurements, which are separated by discrete time intervals, or by continuous measurement. Repeat measurement and continuous measurement are preferred, if it is desired to dynamically detect the binding and unbinding events over time. The change of signal over time is an indication of the association and dissociation kinetics of the respective binding pair (capture probe and ligand) and allows rapid and reliable determination of, for example, the concentration of the ligand in the medium.

The following figures are solely meant to further illustrate the invention but are not meant to limit the scope of the invention disclosed herein and claimed in the appended claims. Furthermore, all references cited are incorporated herein by reference.

Figure 1B:
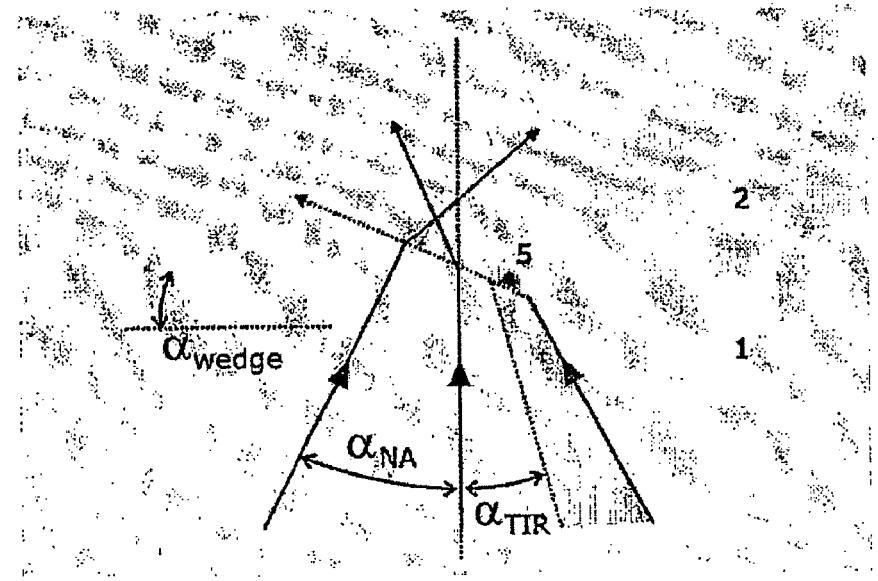

FIG. 1 shows two sections of support of the present invention with three similarly inclined planes adjacent to each other in a "wedged" arrangement. FIG. 1A shows an arrangement in which light directed at the surface of the support at an angle $\alpha_{NA}$, which is not sufficient to allow total internal reflection. Accordingly all light is only refracted at the interface and enters the medium (2) through the support (1). FIG. 1B shows an arrangement in which total internal reflection (TIR) can be achieved at the interface between the support (1) and the medium (2), when the angle $\alpha_{NA}$ of the incoming beam exceeds the value $\beta_{TIR}$-$\alpha_{wedge}$, wherein $\beta_{TIR}$ is the critical angle, given by the equation $\beta_{TIR}=\arcsin(n_{medium}/n_{support})$. This critical angle is approximately 56 degrees for a typical set up in which the support is made of polycarbonate ($n_{disc}$=1.6) and the medium is water ($n_{medium}$=1.33). The part of the light beam for which above condition is met, will exhibit TIR (5), whereas the rest is being refracted and transmitted into the medium. Only if the condition $\alpha_{wedge}-|\alpha_{NA}|>\beta_{TIR}$ is met for the complete beam, then all of the beam will exhibit TIR at the polycarbonate/water interface.

Figure 2:
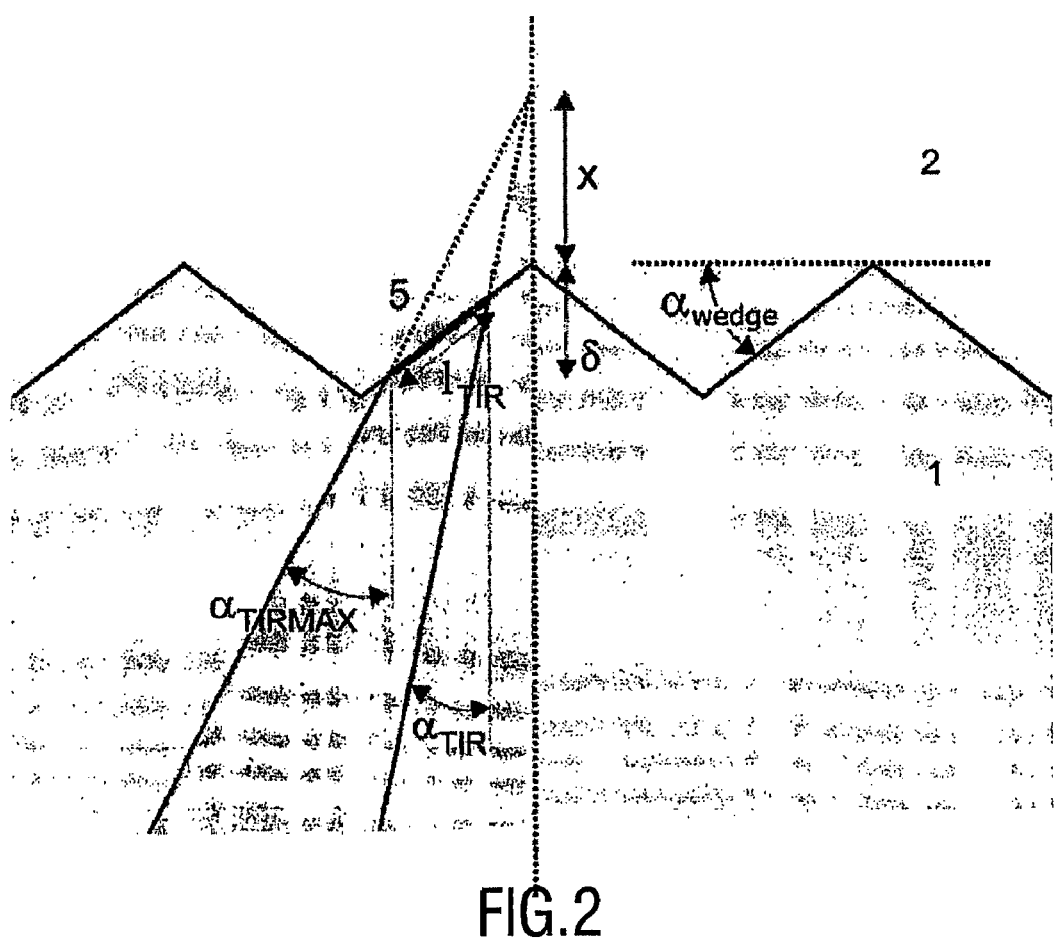
FIG. 2 shows the light path of light directed at the support, which has a focal point behind the surface of the support in accordance with an embodiment of the present invention.

FIG. 2 shows the light path of light directed at the support, which has a focal point behind the surface of the support. The distance of the focal point from the surface of the support is "x" also termed the amount of "defocus", the depth of the inclined plane is "δ", the angle of inclination of the plane is "$\alpha_{wedge}$", "$\alpha_{TIRMAX}$" and "$\alpha_{TIR}$" are the bounding angles for which total internal reflection occurs at the surface of the inclined plane and "$l_{TIR}$" is the length of TIR on the inclined plane, i.e. the TIR active area length. The light is directed through the support (1) to the support medium interface, undergoes TIR and generates an evanescent-field (5) in the medium (2).

FIG. 3 shows an example in which an additional tracking layer is provided in the support which allows the correct alignment of the light with the inclined planes on the surface of the support, even so the beam is "defocused", i.e. has its focal point in the tracking layer within the support. To decrease the amount of light refracted and transmitted into medium (2) an additional intermediate plane is positioned adjacent to the first inclined plane parallel to the lower surface and is provided with a reflective coating (50). The light is directed through a first support structure (11) comprising tracking signals (12) and a second support structure (13) forming the inclined planes on the surface of the support (1). The condition $\alpha_{wedge}-|\alpha_{NA}|>\beta_{TIR}$ is met for all parts of the beam directed at the inclined planes and the part of the beam for which this condition is not met will be reflected back towards the light source at the intermediate plane.

FIG. 4 shows an example where the disc/medium interface is being irradiated by a focussed beam, generated by an objective lens (3). In front of the objective lens an obstructing mask (4) is positioned, such that only those rays are being transmitted that fulfil the condition $\alpha_{NA}>\beta_{TIR}-\alpha_{wedge}$. As a result, no direct refracted light is transmitted into the medium. Only an evanescent wave is coupled into the medium, being located very close (<λ) to the surface (5). The internally reflected beam resulting from the TIR has not been drawn.

FIG. 5 shows an example where the wedge shaped structure has been replaced by a symmetric pyramidal shaped structure. The support/medium interface is being irradiated by two focussed beams, generated by an objective lens (3). In front of the objective lens an obstructing mask (4) is positioned, such that only those rays of the two beams are being transmitted that fulfil the condition $\alpha_{NA} > \beta_{TIR} - \alpha_{wedge}$. In this case TIR occurs at both inclined planes within one measuring area, thereby doubling the total power enclosed in the evanescent-fields formed (5). Furthermore, diffraction at the pyramidal structure gives rise to a symmetric (push-pull) tracking signal for radial tracking of the optical disc. The objective lens NA and size of the mask is determined by the pyramidal wedge angle $\alpha_{wedge}$ and the critical angle $\beta_{TIR}$. In this arrangement measures may need to be taken to avoid transmission of the excitation beam into the fluid after TIR, e.g. by applying absorbing or reflecting coatings at the right locations.

FIG. 6 shows the same set-up as FIG. 5, however the objective lens has been modified such that a central part lens (31), which is partly covered by an obstructive mask (4) provides the light beam eliciting the evanescent-field and is used for the generation of tracking signals, whereas an additional higher-numerical aperture (NA) lens (32) collects the photons emitted by fluorescence of molecules excited by the evanescent-fields (5). As a result the system has a larger acceptance angle, thereby increasing the detection efficiency. The low NA (i) is used for sampling and tracking, while the high NA (i) is used for detection. In case of fluorescence detection, the collection of fluorescence light can also be done by an optical system on the opposite side of the disc.

Figure 7:
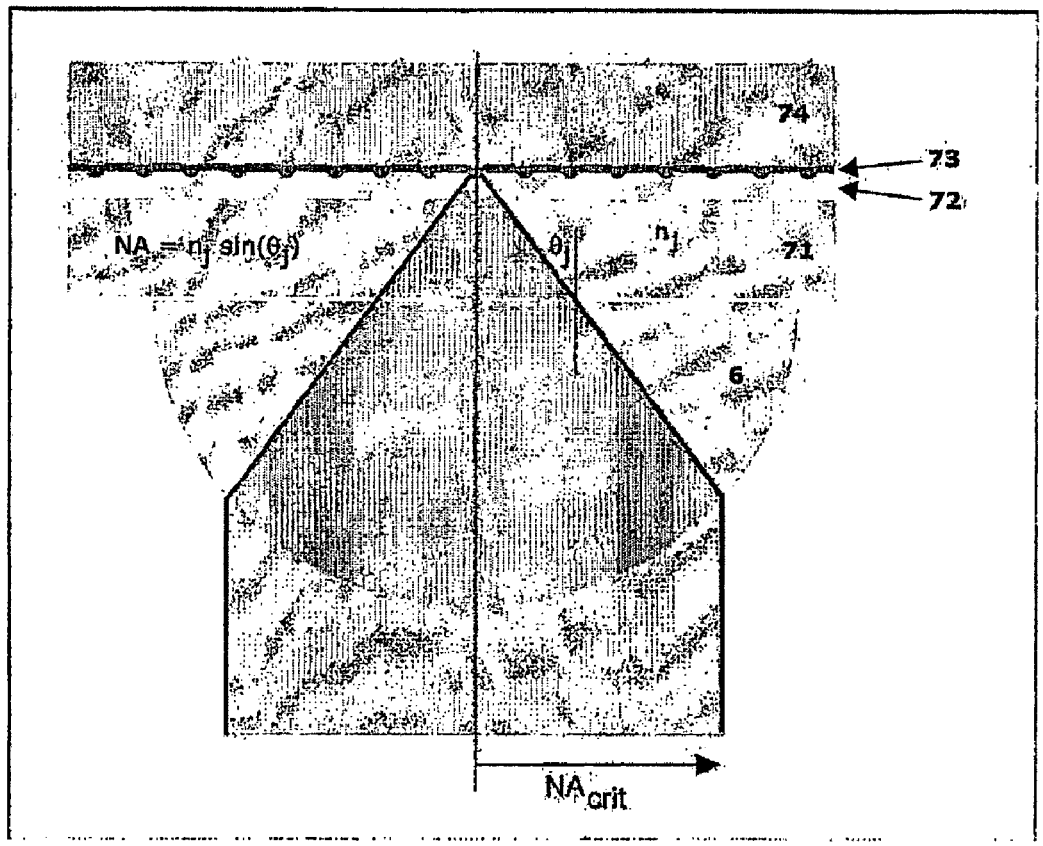
FIG. 7 shows readout of the support using conventional near field coupling, where the objective lens is in close contact with the optical disc in accordance with an embodiment of the present invention.

FIG. 7 shows readout of the support using conventional near field coupling, where the objective lens (6), preferably a near field objective lens, with an NA>1.33 is in close contact (<λ) with the optical disc. The medium(74) preferably is water with n=1.33. A gold film (73) is applied for reflection. The support preferably comprises a polycarbonate (PC) replicated structure comprising the inclined planes (72) and a glass or PC substrate (71) ($n_{support}$=1.5 and 1.6, respectively). As a result a high readout NA can be realized at the support/medium interface. As long as the NA does not exceed the refractive index $n_{medium}$, light is being transmitted at the plastic/water interface and no TIR occurs. For numerical apertures greater than this critical $NA_{crit}$ (=$n_{medium}$) total internal reflection occurs at the polycarbonate replicated structure, giving rise to an evanescent wave coupling into the water medium (see FIG. 8).

Figure 8:
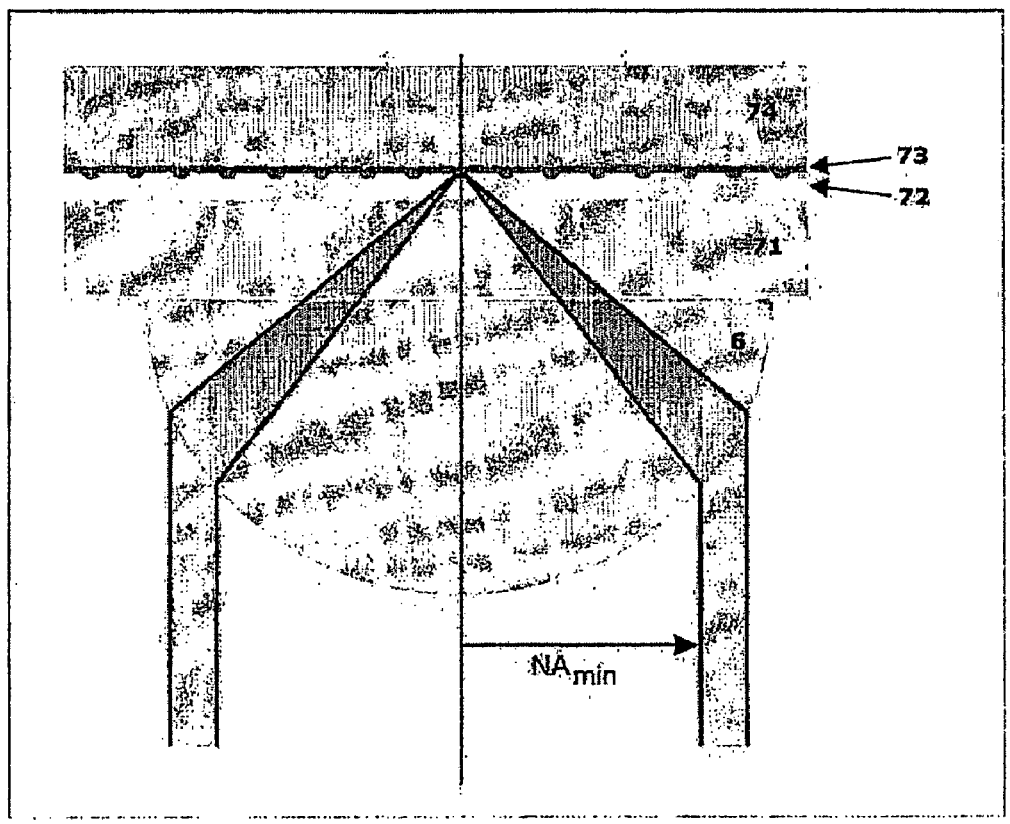
FIG. 8 shows an example in which the numerical aperture of objective lens exceeds the critical angle in accordance with an embodiment of the present invention.

FIG. 8 shows an embodiment of the present invention in which the numerical aperture of objective lens exceeds the critical NA. For entrance angles greater than $NA_{min}$ the incoming light at the support/medium interface is being totally internal reflected (the support contains the wedge structures), giving rise to evanescent wave coupling into the medium. The support comprises a polycarbonate (PC) replicated structure comprising the inclined planes (72) and a glass or PC substrate (71) ($n_{disc}$=1.5 and 1.6, respectively). Instead of a gold layer the surface of the wedge structure is coated with a capture probe layer (73). The medium(74) preferably is water with n=1.33.

Figure 9A:
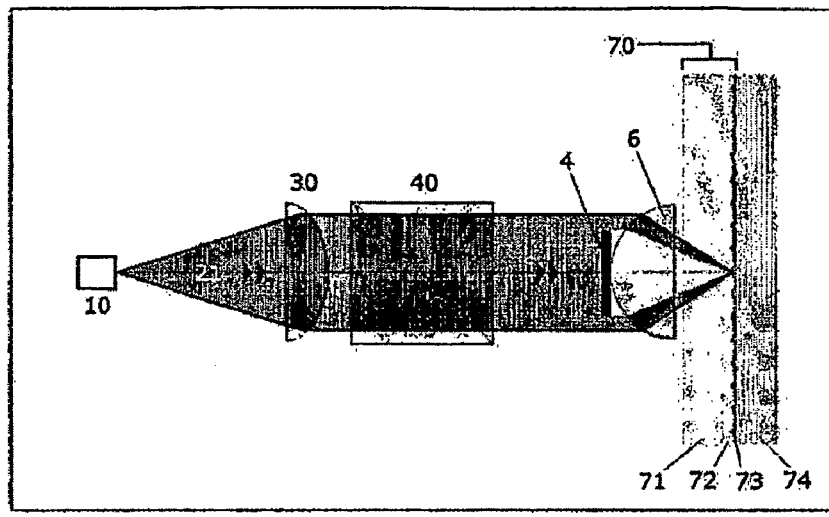
FIG. 9A shows the light path from laser to a disc in which a collimator, a splitter, a mask and an objective are arranged in accordance with an embodiment of the present invention.
Figure 9B:
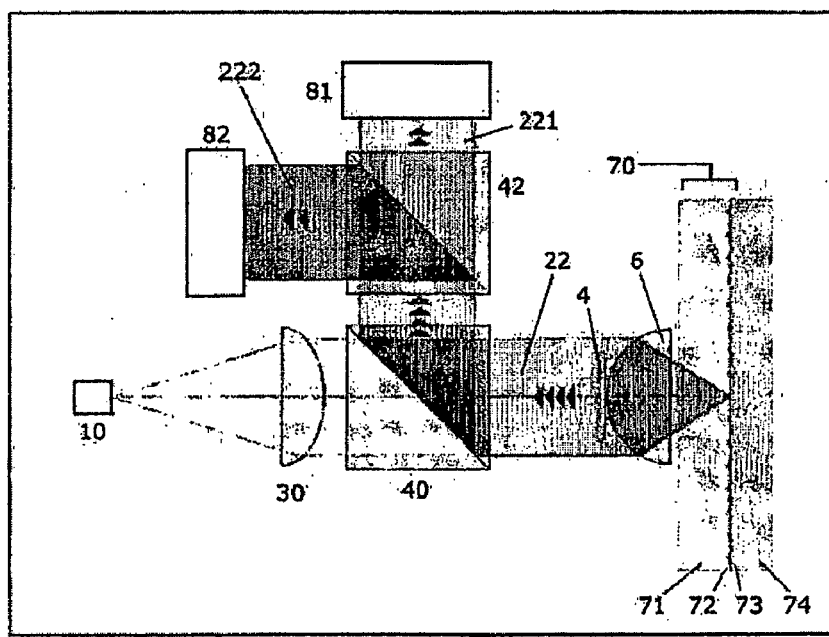
FIG. 9B shows the return light path from support to detector in accordance with an embodiment of the present invention.

FIG. 9 shows an optical recording set-up for readout of the support. FIG. 9A shows the light path (21) from laser (10) to disc (70) in which a collimator (30), a splitter (40), a mask (4) and an objective (6) are arranged. The support material (71) and (72) to which a capture probe (73) is attached, is arranged towards the laser, while the medium containing the ligand (74) is arranged on the opposite side. The set-up includes the obstructive mask (4) for selecting entrance angles such that only those rays are transmitted that give rise to TIR at the disc/medium interface. FIG. 9B shows the return light path (22) from support to detector. A dichroic mirror (42) may be arranged for distinguishing between the directly reflected/diffracted light (222) directed to the servo (82) and the (red-shifted) fluorescence (221) from excited surface molecules directed to the detector (81).

Figure 10A:
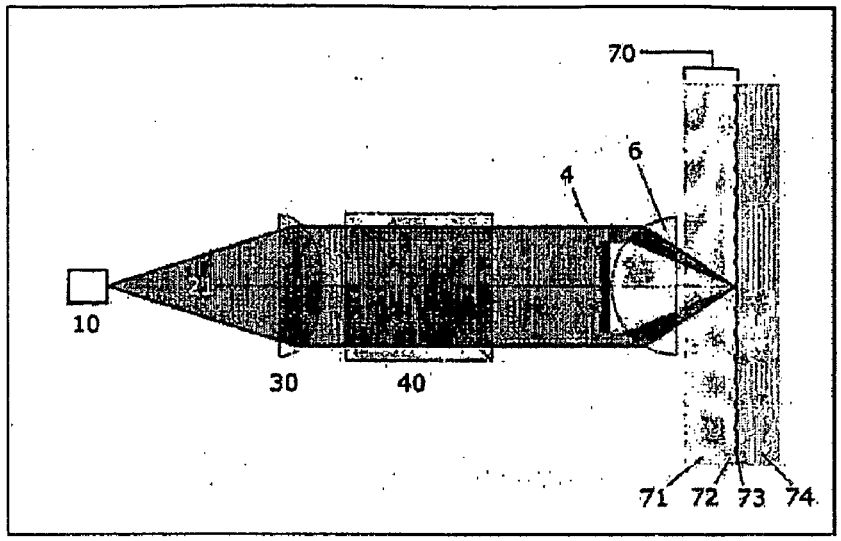
FIGS. 10A, 10B show an alternative arrangement to the one shown in FIGS. 9A, 9B, in which a dichroic structure or polarization sensitive mask is used instead of an obstructive mask in accordance with an embodiment of the present invention.
Figure 10B:
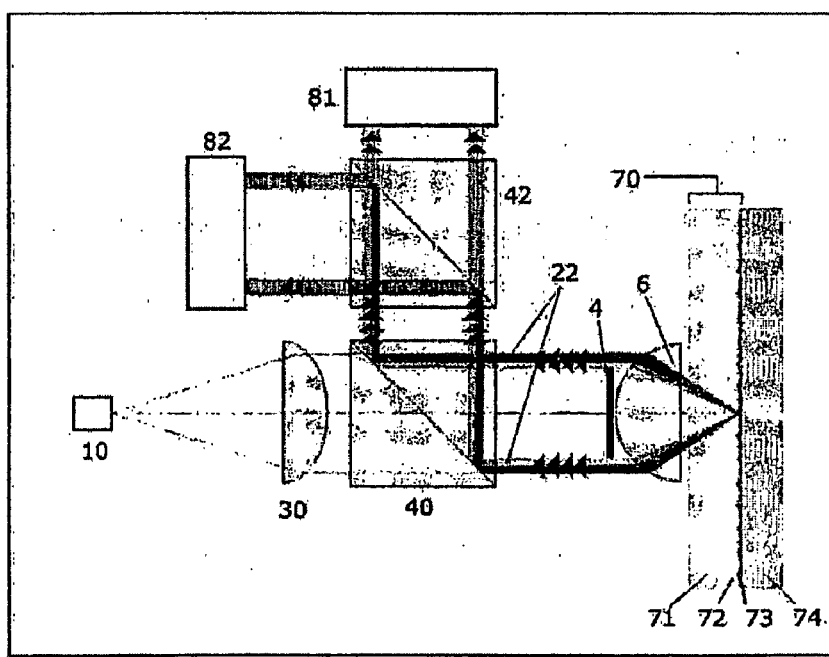

FIG. 10 shows an alternative arrangement to the one shown in FIG. 9 in which a dichroic structure or polarization sensitive mask (4) is used instead of an obstructive mask. As a result all of the reflected fluorescent light that is being emitted in a cone with opening angle equal to the objective NA, is being collected and detected.

Figure 11:
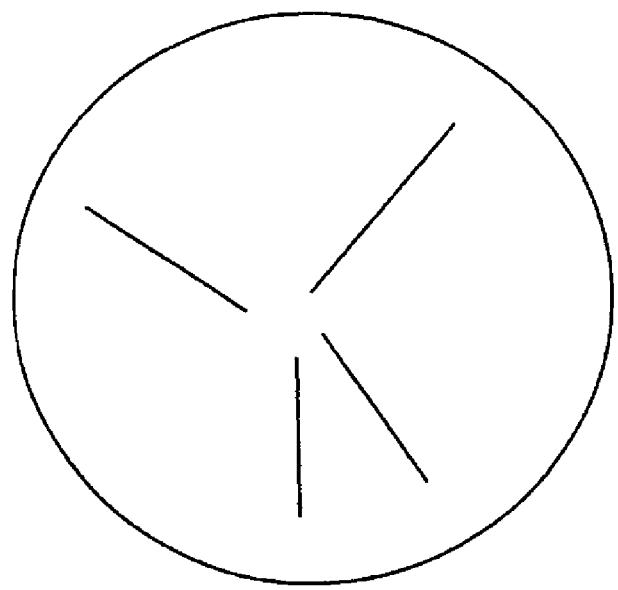
FIG. 11 shows an arrangement of the surface structure of a disc in accordance with an embodiment of the present invention.
Figure 11:
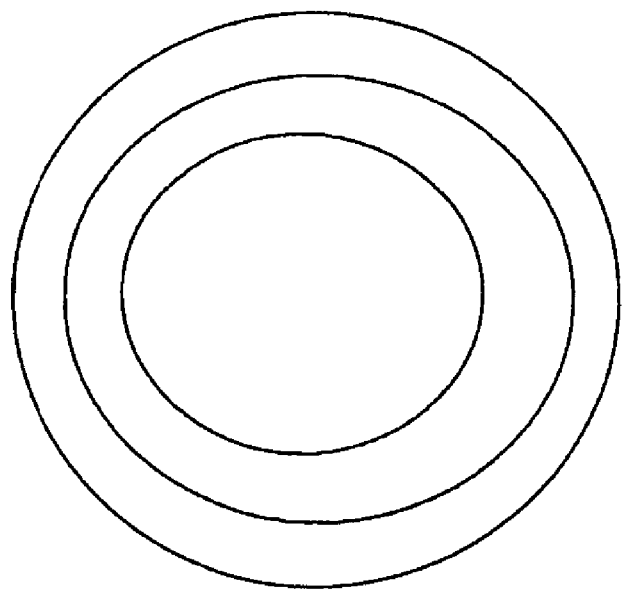

FIG. 11 shows an arrangement of the surface structure of a disc. The areas comprising the inclined planes are structured as channels that extent radial from the center of the disc (A) or structured in circles arranged azimuthal around the center of the disc (B).

The invention claimed is:

1. A support comprising essentially parallel first and second surfaces, wherein at least one area on said first surface comprises surface structures that form evanescent-fields on the first surface of the support for the detection of optically-active substances within the evanescent-fields formed on the first surface of the support, wherein the surface structures on said surface comprise inclined surfaces that are inclined with respect to a plane of the support by an angle within a range from 10° to 85°.

2. The support according to claim 1, wherein the at least one area comprises at least 100 areas.

3. The support according to claim 1, wherein a region of said first surface, where optically-active substances are detected is covered by a top plate.

4. Support according to claim 1, wherein the angle of the inclined surfaces is between 25° and 65°.

5. The support according to claim 1, wherein the refractive index of material forming the support is between 1.4 and 1.8.

6. The support according to claim 1, wherein the surface structures comprise a symmetrical pyramidal structure.

7. The support according to claim 1, wherein at least one capture probe is attached to the surface of the inclined plane.

8. The support according to claim 1, wherein the capture probe is selected from the group comprising antibodies, receptor proteins, enzymes, signaling proteinspeptides, polysaccharides, ssDNA, dsDNA and RNA and PNA.

9. The support according to claim 1, wherein the support further comprises reagents and/or buffers.

10. The support according to claim 1, wherein the support is an optical disc.

11. The support according to claim 1, wherein the support comprises a portion of a kit, wherein the kit comprises at least one of reagents and buffers.

12. A device for the detection of optically-active substances comprising:
  a support having opposing first and second surfaces, wherein the first surface comprises inclined surface structures that form evanescent-fields on the first surface of the support by TIR (total internal reflection) of light;
  at least one light source disposed on a side of the support facing the second surface, to emit the light that is directed at the inclined surface structures on the first surface through the support; and
  at least one detector configured to detect an optically-active substance within an evanescent-field formed by the inclined surface structures on the first surface of the support.

13. The device according to claim 12, wherein the at least one detector is arranged on the same side of the support as the light source.

14. The device according to claim 12, wherein the at least one light source generates essentially monochromatic light.

15. The device according to claim 12, wherein the at least one light source comprises at least two light sources generating essentially monochromatic light of at least two different wavelengths.

16. The device according to claim 12, further comprising a filter arranged within a light path of the at least one light source.

17. The device according to claim 12, further comprising an objective lens configured to focus the light emitted from the at least one light source on the support.

18. The device according to claim 17, further comprising a mask placed in the light path between the light source and the support, which essentially blocks all light directed at the support with an angle that would not result in TIR.

19. The device according to claim 12, wherein the first and second opposing surfaces of the support are essentially parallel and wherein the inclined surface structures are formed in at least one area on the first surface, and wherein the inclined surface structures are inclined with respect to a plane of the support by an angle in a range of 10° to 85°.

20. The device according to claim 19, wherein the support is an optical disc.

21. The device according to claim 19, wherein optical parameters are selected such that a depth d of an evanescent-field, which is formed in a medium comprising the optically active substance applied to the support is between about 20 nm and 200 nm.

22. A method, comprising acts of:
providing a support comprising essentially parallel first and second surfaces wherein at least one area on the first surface comprises surface structures that form evanescent fields on the first surface of the support, wherein the surface structures comprise inclined surfaces that are inclined with respect to a plane of the support by an angle from 10° to 85°; and detecting an optically-active substance within a medium disposed adjacent the first surface of the support using evanescent-fields generated by the surface structures on the first surface of the support.

23. The method according to claim 22, wherein detecting the optically-active substance comprises at least one of detecting fluorescence, detecting optical scattering, and detecting reflectance modulation.

24. The method according to claim 22, wherein the optically-active substance comprises at least one of a ligand labeled with a fluorescence label, a scattering label, and a reflectance modulator.

25. The method according to claim 22, wherein the optically-active substance is contained in or derived from at least one of blood, urine, sperm, vaginal secretion, stool, sputum, tissue, single cells, lymph and contents of a gastrointestinal tract.

26. The method according to claim 22, wherein detecting comprises an act of detecting binding or unbinding of the optically-active substance to the first surface of the support.

* * * * *